United States Patent [19]

Becherucci et al.

[11] Patent Number: 5,696,326

[45] Date of Patent: Dec. 9, 1997

[54] METHOD AND APPARATUS FOR ACOUSTIC TESTING OF ARMATURES

[75] Inventors: Antonio Becherucci; Dalibor Kirov, both of Florence, Italy

[73] Assignee: Axis USA, Inc., Tampa, Fla.

[21] Appl. No.: 476,191

[22] Filed: Jun. 7, 1995

Related U.S. Application Data

[63] Continuation-in-part of Ser. No. 170,427, Dec. 20, 1993, Pat. No. 5,492,013.

[51] Int. Cl.$^6$ .................................................. G01N 29/04
[52] U.S. Cl. ............................. 73/600; 73/588; 73/582
[58] Field of Search .......................... 73/600, 588, 582, 73/644, 579, 629, 622, 602; 340/682, 683; 367/13, 87; 364/508, 571.02, 571.04

[56] References Cited

U.S. PATENT DOCUMENTS

| | | | |
|---|---|---|---|
| 3,726,130 | 4/1973 | Hurlebaus | 73/67.8 R |
| 4,445,360 | 5/1984 | Treder, Jr. | 73/1 DV |
| 4,642,617 | 2/1987 | Thomas et al. | 340/683 |
| 4,655,084 | 4/1987 | Renzel | 73/600 |
| 4,707,687 | 11/1987 | Thomas | 340/683 |
| 4,862,383 | 8/1989 | Koshimizu | 73/600 |
| 4,894,201 | 1/1990 | Ahmed | 73/622 |
| 5,170,367 | 12/1992 | Mackay et al. | 364/571.01 |

*Primary Examiner*—Christine K. Oda
*Attorney, Agent, or Firm*—Fish & Neave; Jeffrey H. Ingerman

[57] ABSTRACT

An objective and non-destructive test of the fused joints in an armature, that can be used on every armature being manufactured on an armature manufacturing line, as well as apparatus for performing that test, are provided. The armature is immersed in an acoustic coupling medium. Acoustic pulses, preferably ultrasonic pulses, are beamed onto the commutator tang/wire interface region of a commutator tang/bar fused joint or the fused joint itself and an acoustic signature is measured. The quality of the joint can be determined by comparing the acoustic signature to a predetermined acoustic signature of known quality. A testing station on an armature production line includes a mechanism for removing the armature from the production line, immersing it in the coupling medium, and rotating it as each joint in the commutator of that armature is checked.

48 Claims, 10 Drawing Sheets

METHOD AND APPARATUS FOR ACOUSTIC TESTING OF ARMATURES

CROSS REFERENCE TO RELATED APPLICATION

This application is a continuation-in-part of commonly assigned U.S. patent application Ser. No. 08/170,427, filed Dec. 20, 1993, now U.S. Pat. No. 5,492,013.

BACKGROUND OF THE INVENTION

This invention relates to the acoustic testing of armatures of dynamoelectric machines. More particularly, this invention relates to the ultrasonic testing of fused joints between the tangs and commutator bars of such an armature.

The armature of a dynamoelectric machine—i.e., of an electric motor or generator—has at least one wire coil wound thereon. Electrical power is conducted to the coils through a commutator which circumscribes the armature shaft and contacts electrical brushes on the stationary part of the dynamoelectric machine. The commutator is made of an even number of commutator "bars" spaced around the shaft. Each end of each coil terminates at a commutator bar.

A commutator bar is generally a substantially rectangular piece of copper. If the number of commutator bars in the commutator is small, each bar may have a slight curvature so that the commutator as a whole is substantially round. Where the number of commutator bars is large, it is not necessary for the bars to be curved.

A commonly employed method for terminating the coil end leads to the commutator bars is to provide on each commutator bar a small finger-like extension known as a "tang." The tang is bent at an angle to form a hook around which the coil lead is wrapped. The tang is then bent over parallel to and touching the commutator bar, so that the lead is trapped. The surfaces of the tang and the commutator bar that are in contact are then joined to prevent the tang from unfolding and freeing the lead.

A common method of joining the tang surface to the commutator bar surface is called "fusing" or "hot-staking." In this method, the surfaces are joined by applying pressure on the tang with a probe, forcing the tang against the commutator bar, and then heating the joint by either heating the probe or passing an electric current from the probe through the joint. The combination of heat and pressure causes projections and depressions on one surface to interengage with depressions and projections on the other surface to form a frictional joint; no significant melting of either surface occurs. In addition, an insulating coating on the wire trapped in the joint vaporizes, allowing the wire to make electrical contact with the commutator bar.

Because of the nature of fusing, fused joints will almost always contain gaps. Usually, these gaps are small "microgaps" dispersed throughout the joint, but larger gaps could also be present. The number, size and distribution of gaps is one indicator of the quality of the fused joint. Joint quality can be measured, for example, by the percentage of the area of the joint that is occupied by gaps; the higher the percentage, the worse the joint.

In practice, however, it has not heretofore been possible to directly measure the gap percentage. Instead, a test known as the "click test" has commonly been used. In the click test, a mechanical probe is manually inserted into the joint by an operator who applies force to break the joint open. The breaking of the joint produces an audible click sound, and the operator is trained to distinguish the sound of a good joint from that of a bad joint. The test is thus highly subjective, leading to variations in quality depending on the operator's perceptions. In addition, the test is destructive, and tested armatures must be discarded. Statistical assumptions must be made with respect to untested armatures, which are the only ones that can be used.

In a refined version of the click test, the probe is equipped with a force gauge, and the force needed to break open the joint is measured. When the force exceeds a threshold, a good joint is indicated. Although this test is more objective, it is still destructive and must rely on statistical assumptions with respect to the untested armatures. Even if the application of force were stopped at some level deemed appropriate (assuming the joint has not opened at a lower level of force), thus saving the armature, such a test would be too slow to use on all armatures. Statistical assumptions would still be required.

The click test is also incapable of measuring other indicators of joint quality. For example, the portion of the tang adjacent the wire should be bent around the wire and in contact with substantially the complete circumference of the wire. If the tang is not bent properly, there may be gaps between the tang and the wire, so that electrical contact and mechanical strength are compromised. In addition, the gaps may contain residual unmelted or partially vaporized and redeposited insulation. The presence of insulation in the gaps at the wire/commutator tang interface region indicates that the heat or pressure applied by the fusing apparatus to the joint during the fusing process was inadequate, and thus likely produced a joint of unacceptable quality.

The heat and pressure applied during the fusing process also ideally causes some deformation of the wire within the bent commutator tang. Insufficient wire deformation indicates insufficient applied pressure or heat. Excessive wire deformation indicates excessive pressure or heat. The click test and its variants do not measure any characteristic of the wire/commutator tang interface region.

Thus, it would be desirable to be able to provide an objective and non-destructive test of the fused tang/commutator bar joints in an armature.

It would also be desirable to be able to provide an objective and non-destructive test of the wire/commutator tang interface region in a fused tang/commutator bar joint in an armature.

It would further be desirable to be able to provide such tests that could be used, if desired, on every armature being manufactured on an armature manufacturing line.

SUMMARY OF THE INVENTION

It is an object of this invention to provide an objective and non-destructive test of the fused tang/commutator bar joints in an armature.

It is also an object of this invention to provide an objective and non-destructive test of the wire/commutator tang interface region in a fused tang/commutator bar joint in an armature.

It is a further object of this invention to provide such tests that could be used, if desired, on every armature being manufactured on an armature manufacturing line.

In accordance with the present invention, there is provided a method for testing the quality of a fused joint between a commutator tang and a commutator bar in a commutator of an armature of a dynamoelectric machine. The test includes directing an acoustic beam comprising at least one acoustic pulse toward said second tang surface along an axis substantially perpendicular to said second tang surface. At least a portion of each pulse passes through said tang and reflects off either the fused joint or the interface region. The acoustic signature, consisting of the reflected portion of each pulse, is measured. The quality of the fused joint is determined by comparing the acoustic signature to signatures of known joint quality. If the signature is substantially similar to signatures of acceptable joint quality, the fused joint is characterized as acceptable. Also, if the signature is substantially similar to signatures of unacceptable joint quality, the fused joint is characterized as unacceptable.

Apparatus for carrying out these methods, as well as armature testing stations incorporating the apparatus, are also provided.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which.

DETAILED DESCRIPTION OF THE INVENTION

The present invention uses an acoustic beam, preferably an ultrasonic beam, to test fused tang/commutator bar joints. The quality of the joint is determined by measuring the reflected acoustic signature of the ultrasonic beam from the joint or from the wire/commutator tang interface region of the joint.

As discussed above, a fused joint is formed by the interlocking of the projections and depressions in the surfaces being joined. In a theoretically "perfect" joint, every projection finds a depression to fill, and every depression is filled by a projection, with no gaps whatsoever in the structure. Such a joint would appear to the ultrasonic beam as a continuous mass of metal, and as such would be transparent to the beam, generating no reflection. At the other extreme, the worst possible joint is one which is completely open. Such a joint would reflect a maximum amount of the beam, producing an acoustic signature with a maximum reflected amplitude, although because of attenuation, the reflected amplitude received at the probe would not be expected to equal the amplitude of the original beam transmitted from the probe, even if 100% of the beam were reflected.

In practice, actual fused joints are neither theoretically perfect, nor are they open. Instead, they contain some percentage of gaps or unjoined areas. Thus, the acoustic signature will contain a reflected beam amplitude that will range between above about zero and below about the original amplitude; the more gaps there are in the joint, the greater the reflected amplitude will be.

In fact, even a joint considered "perfect," or the best attainable joint, in practice, may contain some open area. Specifically, for certain types of tangs, it may be possible to achieve a joint with no measurable open area, other than microgaps. However, for other types of tangs, there may be about 25% open area—i.e., the two sides of the joint are not touching in approximately 25% of the area of the joint as measured in the plane of the joint. For still other types of tangs, the joint may have a different amount of open area. It has been found empirically that a joint can have up to about 75% open area and still be acceptable. It has also been found empirically that the amplitude of the reflected signal within the acoustic signature can be made directly proportional to the open area.

Specifically, at a preferred frequency of about 20 MHz, for a particular type of copper tang of the size used in small electric motors, measured in the acoustic coupling medium described below, the reflected amplitude has been found to be directly proportional to the amount of open area resulting from gaps having a depth greater than about 0.005 mm perpendicular to the plane of the joint. Although there may also be microgaps having a depth less than about 0.005 mm that do not contribute significantly to the reflected amplitude, such microgaps are not of concern in assessing the quality of the joint, and thus the reflected amplitude can be used as a measure of the open area.

By measuring a known "perfect" joint, one can obtain a minimum expected reflected amplitude (corresponding to the amount of open area). Similarly, by measuring a totally open joint, one can obtain a maximum expected reflected amplitude (corresponding to about 100% open area). For gaps of interest (i.e., those greater in depth than about 0.005 mm when a probe frequency of 20 MHz is used for the particular type of tang discussed above), the gap area, or open area, can be determined by linearly interpolating the reflected amplitude between the minimum and maximum expected amplitudes.

In addition to the presence of microgaps at the joint, gaps may also be present at the wire/commutator tang interface region in a fused tang/commutator bar joint of an armature. Sometimes the gaps are not empty (i.e., filled with air) but contain residue from the fusing process. For instance, gaps at the wire/commutator tang interface region may contain residual unmelted or partially vaporized and redeposited insulation. As will be more fully discussed below, the content of the gap is an indicator of the joint quality and can be determined by analyzing the acoustic signature of the reflected portion of the transmitted acoustic beam.

Another indicator of the quality of a fused tang/commutator bar joint is the degree of wire deformation that occurred during fusing. During the fusing operation, heat and pressure are applied to the joint in accordance with a predetermined electrical delivery function so that the commutator tang is softened and at least partially wrapped around the armature wire and so that insulation on a portion of the wire within the softened deformed commutator tang is vaporized. If the acoustic signature of the wire/commutator tang interface region indicates that the wire has been excessively deformed, this may in turn indicate that excessive heat or pressure was applied during the fusing process. If, on the other hand, the acoustic signature indicates that the wire was not sufficiently deformed, this may in turn indicate that insufficient heat or pressure was applied during the fusing process, possibly also indicating that the wire and commutator tang were not in intimate contact during the fusing process. Therefore, the degree of wire deformation in the wire/commutator tang interface region in a fused tang/commutator bar joint is another indicator of joint quality.

By measuring the acoustic signature of joints of known quality, it is possible to determine a series of standard signatures to which an acoustic signature of unknown joint quality can be compared. In this way, an accurate determination the quality of the joint can be made. For example, the acoustic signature of the interface region can reveal the presence of gaps, the contents of the gaps, and the degree of wire deformation at that interface region. Therefore, it is possible to accurately determine the quality of a fused tang/commutator bar joint by examining the acoustic signature of a wire/commutator tang interface region.

As discussed above, if a gap exists in the wire/commutator tang interface region of a fused tang/commutator bar joint, a portion of each transmitted pulse will reflect off the interface region, yielding at least one reflected peak in the acoustic signature. If the acoustic frequency is increased or the size of the gap is large, two distinguishable peaks reflect from a single interface region. This double reflection occurs because the gapped interface region is actually comprised of two interfaces, each capable of individually reflecting a portion of each acoustic pulse. From each reflected portion, a single reflected amplitude can be determined.

The amplitudes and round-trip times of the two reflected portions in the acoustic signature indicate the size and content of the gap. For example, if the interface region contains an air gap, it actually consists of two metal-air interfaces. Alternatively, the gap may be filled with wire insulation which did not fully vaporize, in which case the interface region consists of two metal-insulation interfaces. The pair of interfaces yield a pair of reflected peaks in the acoustic signature, each with its own amplitude and round-trip time. The difference between the round-trip times indicates the depth of the gap. The amplitudes, optionally in combination with the round-trip times, can indicate the content of the gap. Therefore, if two gaps have different contents or depths, the acoustic signatures would be distinguishable.

In a testing apparatus according to the invention, it is preferred that an acoustic probe, preferably ultrasonic, having both an emitter and a receiver be used. The probe would be aimed at the outer surface of the tang along an axis substantially perpendicular to the outer surface of the tang (and to the joint) so that the reflection returns to the receiver in the probe. Such probes are available in both focused and unfocused varieties, with the difference for purposes of the present invention being in how far from the test area the probe can be and still be focused on the tang without spilling onto adjacent areas. An unfocused probe can be further from the surface than a focused probe. A preferred probe is a focused probe because it is easier to align the probe perpendicularly to the joint when it is closer to the test area.

It is also preferred that the probe and the test sample be immersed in a medium having an acoustic conductivity higher than that of air, for better coupling of the beam to the sample. The acoustic coupling medium should also preferably be electrically nonconductive so that any residue that may remain on the sample does not adversely affect performance of the dynamoelectric machine in which it is installed. Similarly, the acoustic coupling medium preferably should not oxidize any part of the armature. One particularly preferred medium is sold as an environmentally safe cleaning and degreasing agent for electrical and electronic components under the name "KEMPT" by the Chemsearch division of NCH, of Milan, Italy.

The selection of a frequency for the probe beam depends on the area and depth of the gaps expected in the joints to be tested, the material of the tang, the thickness of the tang, and the coupling medium. As set forth above, a frequency of about 20 MHz is preferred for one particular type of copper tang used in small electric motors, tested in the KEMPT medium described above.

A preferred embodiment of a testing station on an armature production line, for testing fused joints in accordance with the present invention, would have a device, such as a collet mechanism, for removing the armature to be tested from the production line conveyor and placing it in a vessel filled with acoustic coupling medium. The ultrasonic probe preferably would already be in the vessel. The collet mechanism would be adjusted so that the armature is inserted in the vessel with the surface of a tang, the joint of which is to be tested, aligned perpendicularly to the axis of the probe. Preferably, the collet would be capable of rotating the armature, so that more than one, and preferably all, of the fused joints on an armature could be tested individually. Such a station could be used to test a fraction of the armatures produced by the production line, either at regular intervals or on a random basis, or could be used to test all of the armatures produced. In the latter case, if a single testing station operated too slowly to keep up with the remainder of the production line, a number of identical testing stations could be provided to operate in parallel. The advantages of testing all armatures, without resorting to statistical analysis, is apparent.

In any event, the testing station would relay its results to the production line control unit, which would take appropriate action. For instance, if all armatures were being tested, the appropriate action would be to divert any armature with substandard fused joints to a station at which it could be discarded, or re-fused using modified fusing parameters. The production line might also be stopped for adjustment, especially if more than one armature tested within a certain time period was determined to have substandard tang/ commutator joints. Even if a statistical approach were employed (i.e., if only certain armatures were being tested, a response to a series of substandard joints might be to stop the production line for adjustment.

Preferably, however, the production line would not be stopped and the results gathered by the production line control unit would be processed to cause the unit to continuously or intermittently modify the fusing parameters (i.e., fusing electrode force, speed, or displacement and fusing current) that make up a predetermined fusing profile. An example of an apparatus which continuously monitors and adjusts electrode force or electrode displacement, or both, according to a predetermined function is described in commonly assigned U.S. Pat. No. 5,063,279, which is hereby incorporated by reference in its entirety. Another example of an apparatus that uses profiles to fuse together electrical conductors is described in commonly assigned U.S. Pat. No. 5,300,753, which is also hereby incorporated by reference in its entirety. By continuously modifying the fusing parameters in accordance with the acoustic measurements described above, consistent and high quality fused joints may be produced without stopping the production line.

The theoretical principles of the present invention are illustrated in FIGS. 1–12.

Figure 1:
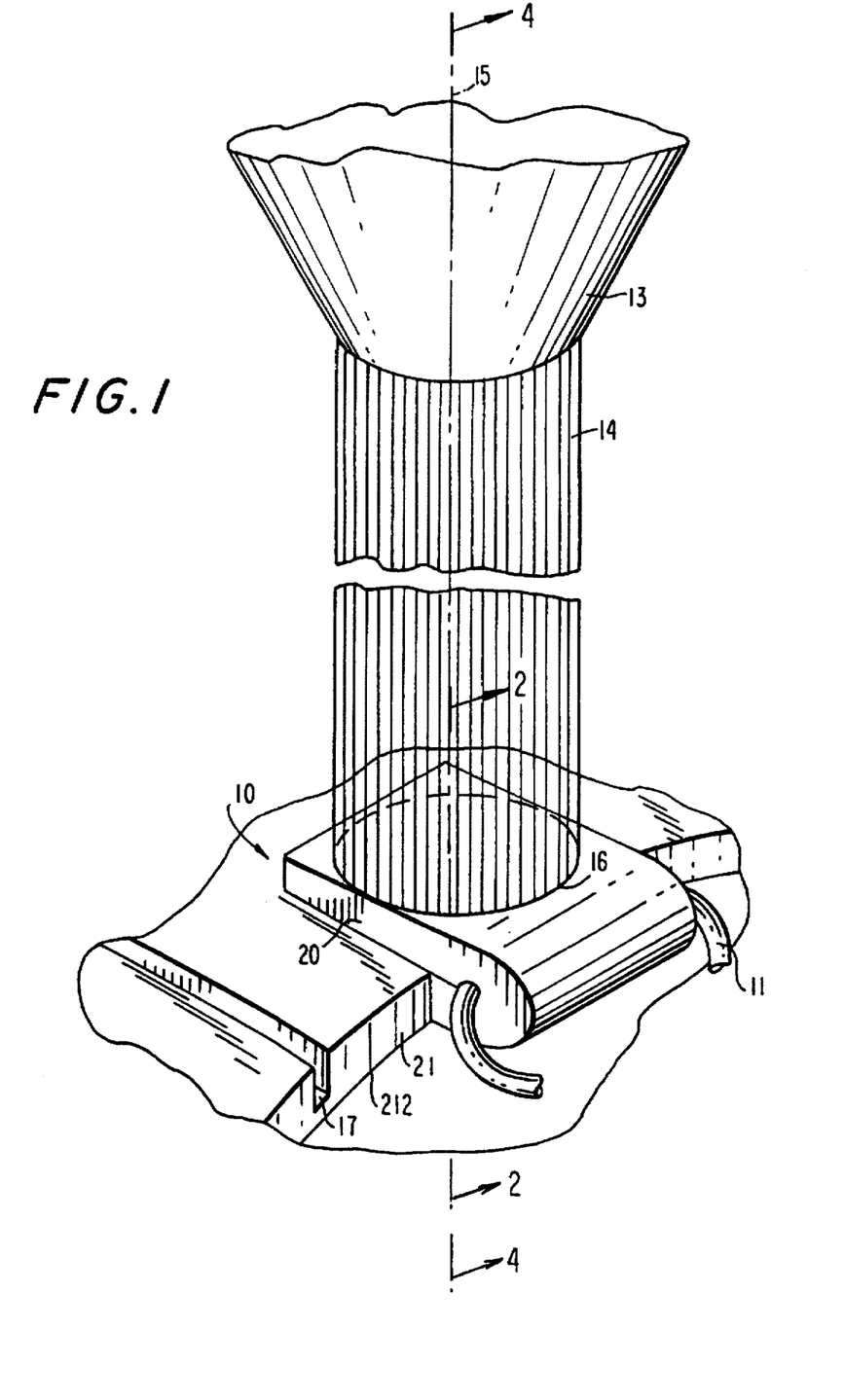
FIG. 1 is a fragmentary perspective view of a fused tang/commutator joint being tested in accordance with the present invention.
Figure 2:
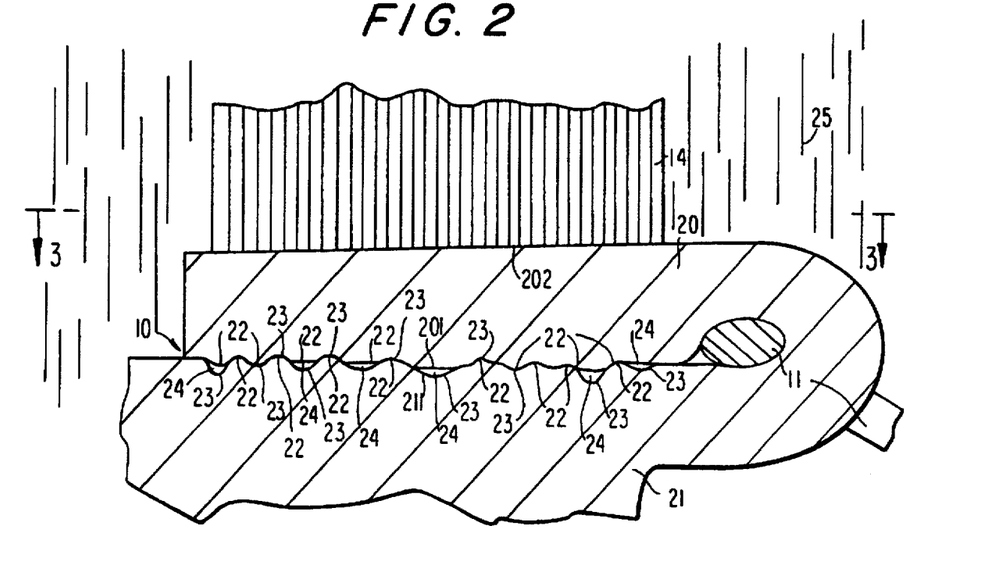
FIG. 2 is a cross-sectional view of a fused tang/commutator joint being tested in accordance with the present invention, taken from line 2—2 of FIG. 1.
Figure 3:
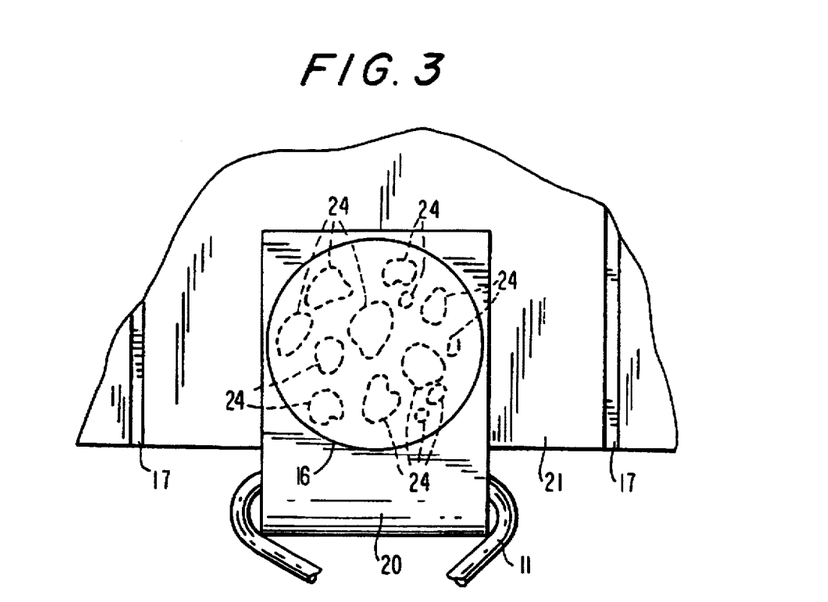
FIG. 3 is a plan view of a fused tang/commutator joint, taken from line 3—3 of FIG. 2.
Figure 4:
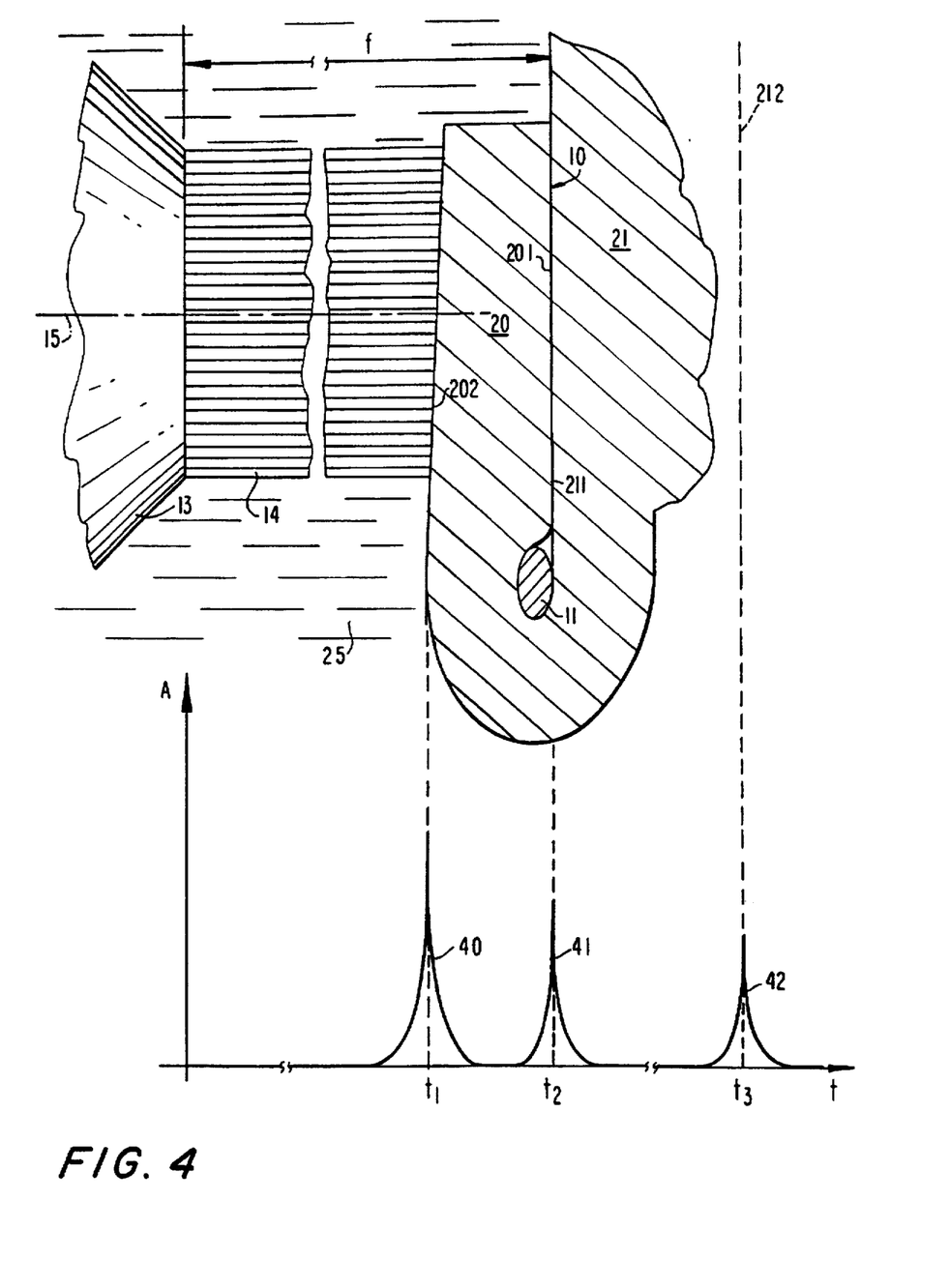
FIG. 4 is a fragmentary cross-sectional view of fused tang/commutator joint being tested in accordance with the present invention, taken from line 4—4 of FIG. 1, showing a graphical representation of the acoustic signature reflected by the joint.
Figure 5:
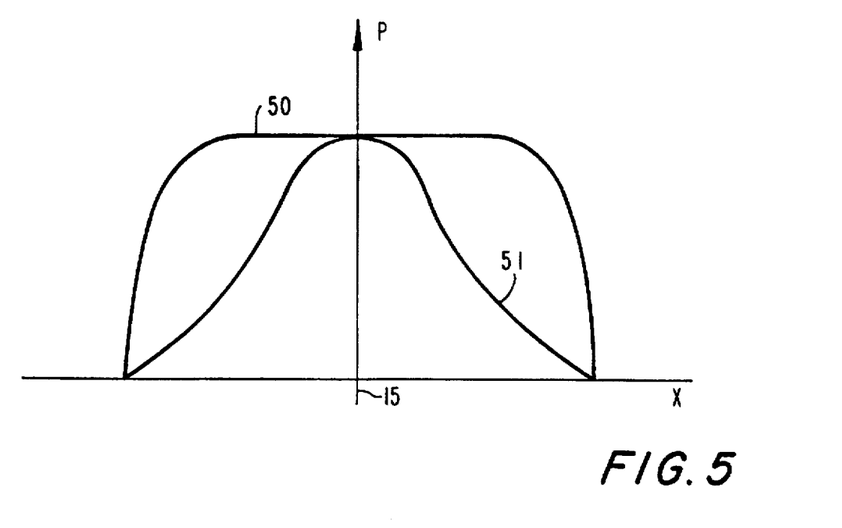
FIG. 5 is a graph showing the pressure distributions for two different acoustic probes of the type used in the present invention.

As shown in FIGS. 1–4 and 6, a fused tang/commutator joint 10 to be tested is formed where tang 20 is folded over onto commutator bar 21 and first surface 201 of tang 20 is fused to first surface 211 of commutator bar 21. While both surfaces 201, 202 of tang 20, and both surfaces 211, 212 of commutator bar 21, appear to the naked eye to be smooth, as illustrated in FIGS. 1 and 4, they are in fact full of projections and depressions as illustrated in FIG. 2. The projections 22 and depressions 23, shown in exaggerated form in FIG. 2, interengage as described above to form joint 10, and also leave gaps 24 as described above (visible in FIG. 2 only). Wire 11 is captured in joint 10.

An ultrasonic probe 13 projects an ultrasonic beam 14 along an axis 15 substantially perpendicular to second tang surface 202. Probe 13 also contains a receiver. The spacing of probe 13 from joint 10, and the configuration of beam 14, are chosen so that the outer contour 16 of beam 14 falls entirely on joint 10, avoiding false echoes from the background 17. As discussed above, beam 14 preferably propagates through an acoustic coupling medium 25. Beam 14 is actually a series of acoustic pulses, each preferably having a pressure distribution about axis 15 as shown at 50 in FIG. 5, so that as strong a signal as possible is generated across the entire joint 10. A pressure distribution such as that shown at 51 is less preferred.

As shown in FIG. 4, the system of the invention transmits acoustic pulses at times spaced apart sufficiently for each pulse to return to probe 13 before the next pulse is sent. The spacing is based on the expected maximum round-trip time for a pulse. Each pulse in beam 14 is partially reflected by surface 202, giving rise to a detected pulse 40 at a time interval $t_1$ from the time of transmission, which is correlated to the distance between probe 13 and surface 202. Some portion of each pulse passes through surface 202 and reflects off gaps 24 in joint 10, giving rise to a detected pulse 41 at a time interval $t_2$ from the time of transmission, which is correlated to the distance between probe 13 and joint 10. Finally, some portion of each pulse passes through joint 10 (either because it impinges on joint 10 where there is no gap 24, or because a portion of the pulse impinging on gap 24 is able to pass through gap 24) and reflects off second surface 212 of commutator bar 21, giving rise to a detected pulse 42 at a time interval $t_3$ from the time of transmission, which is correlated to the distance between probe 13 and second surface 212. There are also effects caused by secondary reflections at each surface, but those can be ignored. The acoustic signature in FIG. 4 plots received amplitude A as a function of time t from transmission, with probe 13 spaced a distance f from joint 10, where f is the focal length of probe 13 (i.e., joint 10 lies in the focal plane of probe 13).

Figure 6A:
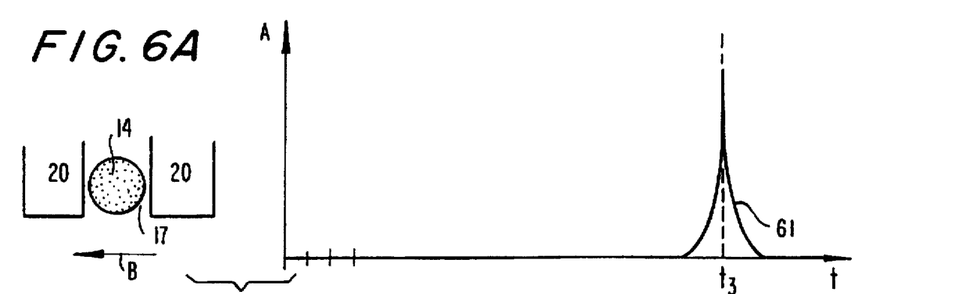
FIGS. 6A–6D are schematic representations of the acoustic beam of the present invention as it scans different locations between two adjacent joints, showing a graphical representation of the acoustic signature reflected at each location.
Figure 6B:
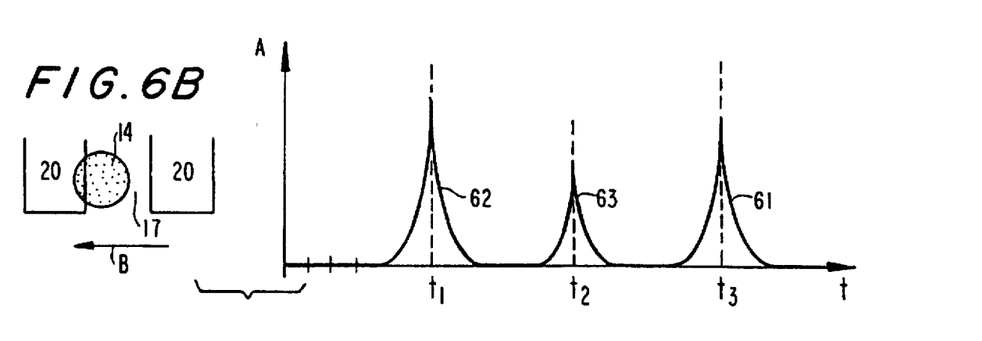
Figure 6C:
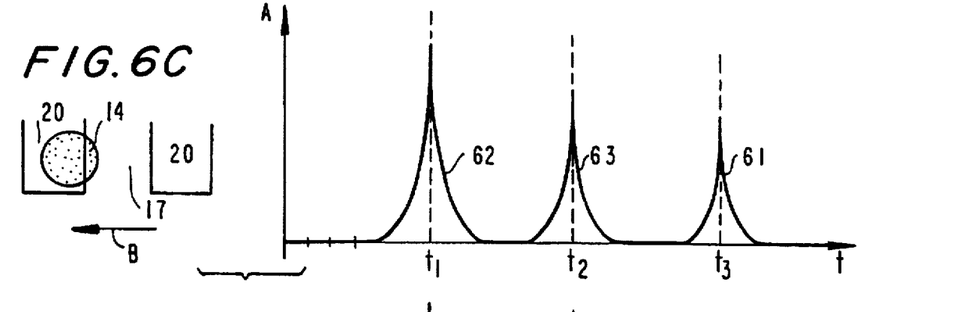
Figure 6D:
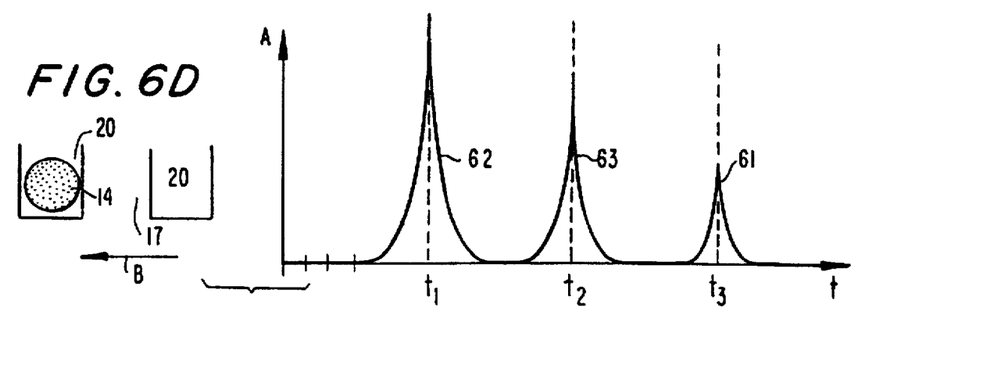

The effects of the various surfaces, as well as the need to have beam 14 aimed squarely at joint 10, is illustrated in FIGS. 6A–6D. In FIG. 6A, beam 14 is aimed at background 17 between two tangs 20. The corresponding acoustic signature 60 of reflected amplitude A versus time t shows a single pulse 61 corresponding to background 17. In FIG. 6B, beam 14 has moved in the direction of arrow B so that it partially impinges on one of tangs 20. In addition to pulse 61, whose amplitude is now diminished as other surfaces reduce the portion of beam 14 reaching surface 17, there are now pulses 61, 63 corresponding to surface 202 and joint 10. In FIG. 6C, beam 14 is almost completely aimed at one tang 20, and pulse 61 is further diminished while pulses 62, 63 have grown. Finally, in FIG. 6D, beam 14 is fully aimed at one tang 20, and pulses 61, 62, 63 have assumed the relative amplitudes seen in FIG. 4. Thus, it is important for accurate results that beam 14 be properly aimed. At the same time, the beam should not be limited to too small an area of joint 10, lest it miss too many of the gaps in the joint. Alternatively, a small beam could be used to separately measure small areas of the joint, and the individual reflected amplitudes could be integrated over the entire joint to give a reflected amplitude for the joint.

The peak of interest is peak 41, which represents the reflection off joint 10. As described above, minimum and maximum expected amplitudes of pulse 41 can be determined by calibrating a testing apparatus according to the invention against a known "perfect" joint (some known amount of open area) and a fully open joint (100% open area). For the conditions described above with respect to the material and thickness of tangs 20, the type of acoustic coupling medium used, and the acoustic frequency, the amplitude of pulse 41 is directly proportional to the amount of open area in joint 10, and thus the amount of open area can be determined by linear interpolation of the amplitude between the expected extrema. In practice, one may not be concerned with determining what the precise open area is. Instead, one may want to know merely whether the amount of open area is above or below a threshold deemed acceptable, so as to determine whether or not the quality of the joint is acceptable. This threshold would be predetermined by interpolation between the extrema based on the minimum acceptable open area.

In addition to comparing a reflected amplitude of a joint of unknown quality to a predetermined threshold amplitude of a joint of known quality, a more general acoustic signature comparison test may also be used. In particular, in such a test an acoustic signature including relevant portions of a reflected acoustic pulse is compared to predetermined acoustic signatures of joints of known quality. If the acoustic signature of unknown joint quality is substantially similar to any of the predetermined signatures, the quality of the joint can be determined.

Figure 7:
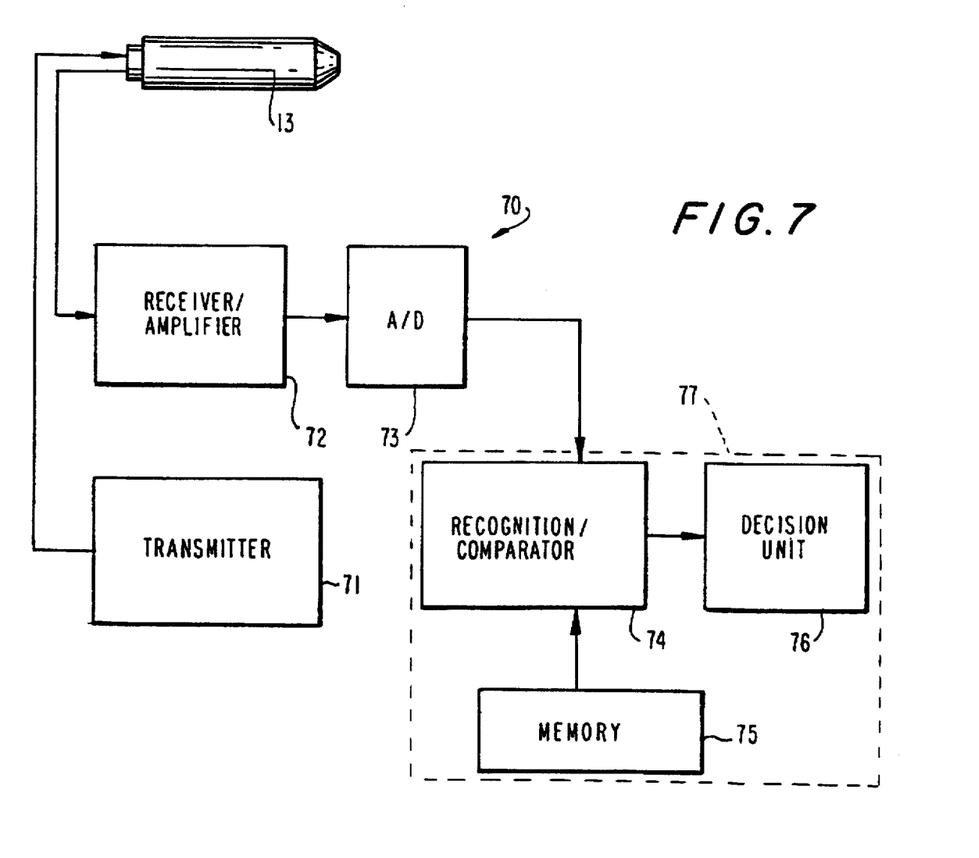
FIG. 7 is a schematic diagram of a preferred embodiment of testing apparatus according to the present invention.

A schematic diagram of apparatus 70 according to the invention is shown in FIG. 7. Apparatus 70 includes probe 13. A transmitter 71 supplies the ultrasonic or other acoustic pulses to be emitted by probe 13. The frequency of transmitter 71 is determined by the desired frequency to be emitted.

Signals representing reflected pulses received by probe 13 are fed to receiver/amplifier 72, which passes them through an analog-to-digital converter 73. The digital signals from A/D converter 73 are passed to processor 77 including recognition/comparator unit 74, memory 75, and decision unit 76. Recognition/comparator unit 74 compares the digital signals, as described above, to signal patterns obtained from joints of known quality and stored in memory 75, or to a threshold stored in memory 75. The result of the comparison is passed to decision unit 76 which determines whether or not the joint is acceptable. As stated above, the output of unit 76 can be used to reject an armature, and discard it or require that it be re-fused.

Figure 8:
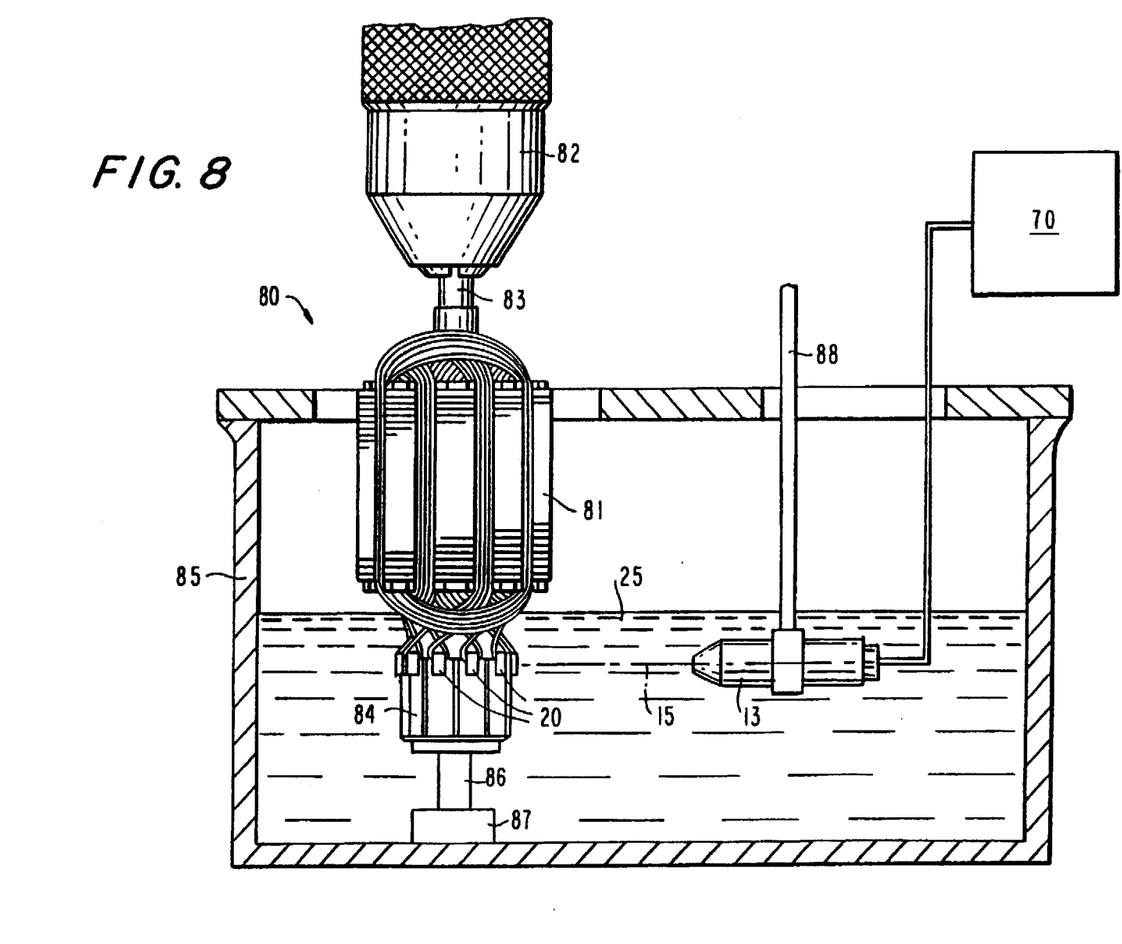
FIG. 8 is a side elevational view, partly in cross section, of a testing station according to the present invention.

An armature testing station 80 according to the invention for an armature production line is shown in FIG. 8. Armature 81 is removed from the production line conveyor (not shown) by collet mechanism 82 which engages end 83 of the armature shaft. Mechanism 82 immerses at least the commutator 84 of armature 81 in acoustic coupling medium 25 in a tank 85. The other end 86 of the armature shaft is rested in a support 87 at the bottom of tank 85. Probe 13 is suspended in tank 85 on arm 88, immersed in medium 25, and is connected by cable 89 to control circuitry 70. Arm 88 is preferably adjustable (not shown) so that axis 15 of probe 13 can be aligned with tangs 20 regardless of the size of armature 81. An appropriate aligning device (not shown) assures that the surface of one of tangs 20 is substantially perpendicular to axis 15.

Preferably, collet 82 is rotatable and support 87 allows rotation, so that armature 81 can be indexed to bring each of its fused joints in line with beam 14 for testing, as described above. Alternatively, instead of indexing armature 81, which adds time as rotation is stopped and started, armature 81 could be rotated continuously. In that case, beam 14 would scan over all the joints 10 in the manner shown in FIGS. 6A–6D. The peak at $t_2$, corresponding to joint quality, would rise and fall during the scanning process as joints moved in and out of beam 14. By monitoring the periodic maxima of the peak at $t_2$, one would be able to determine the quality for each joint, as long as one kept track of which maximum of the peak corresponded to which joint 10. Station 80 might also have more than one probe 13—e.g., three probes at 120° intervals around the armature—to shorten the time necessary to test all joints in a single armature. However, such an arrangement would increase the cost and complexity of station 80.

Figure 9:
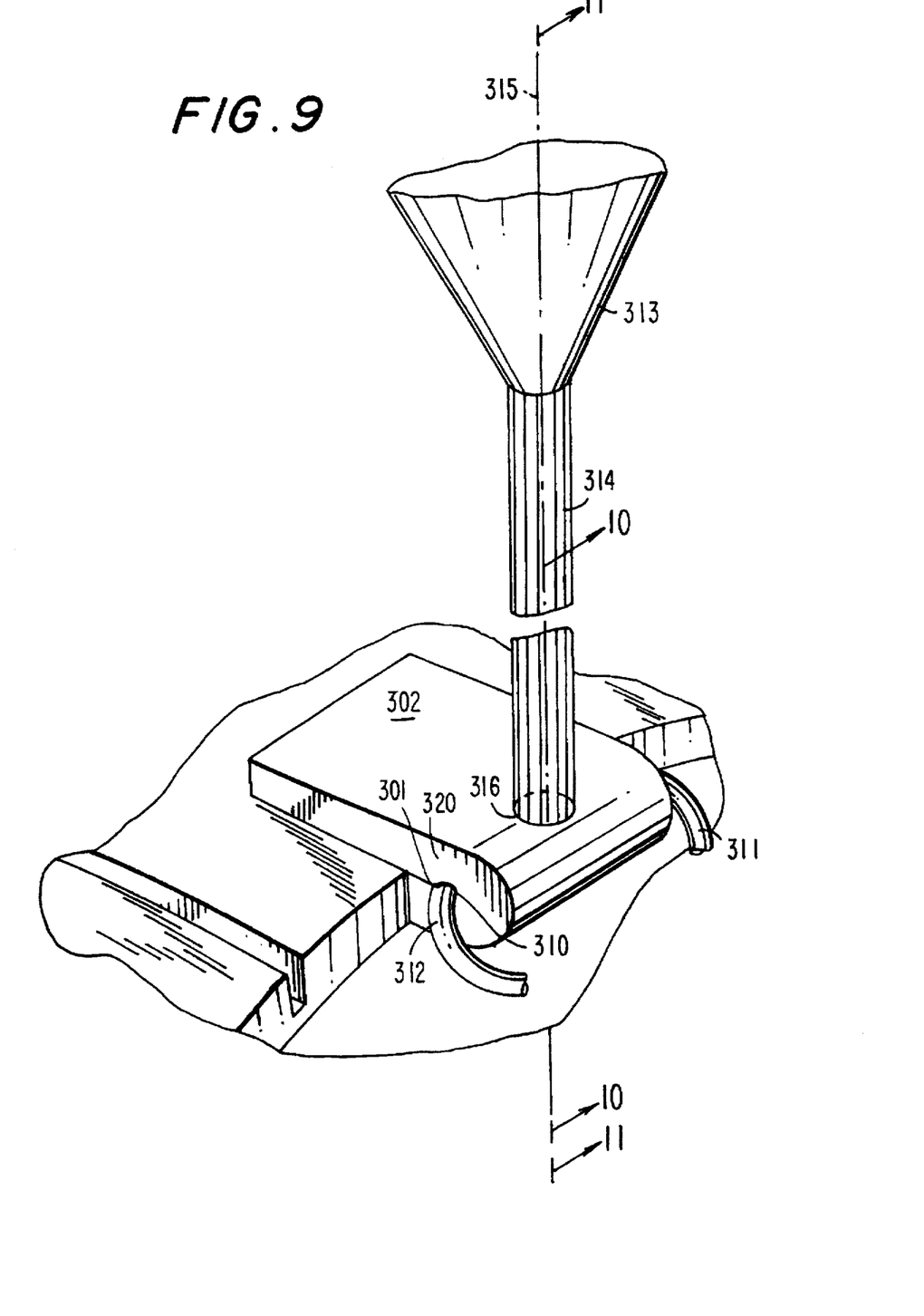
FIG. 9 is a fragmentary perspective view of a wire/commutator tang interface region being tested in accordance with the present invention.

FIGS. 9–12 illustrate a use of the present invention in accordance with the theoretical principles described herein. FIG. 9, for example, shows acoustic beam 314 testing wire/commutator tang interface region 310 of a tang/commutator bar fused joint. Interface region 310 is formed by wrapping tang 320 around wire 311, with first tang surface 301 of tang 320 at least partially in contact with wire surface 312. Second opposing surface 302 of tang 320 is substantially parallel to first tang surface 301. Gaps 324 and 370 are formed at the interface region 310 during fusing and are shown in exaggerated form in FIGS. 10–12.

An ultrasonic probe 313 projects an ultrasonic beam 314 comprising of a plurality of acoustic pulses along an axis 315 substantially perpendicular to second tang surface 302.

Gaps 324, like gaps 24 shown in FIGS. 2 and 3, cause a portion of each pulse to be reflected backwards and detected by an acoustic receiver, preferably located in probe 313. The spacing of probe 313 from interface region 310, and the configuration of beam 314, are chosen so that the outer contour 316 of beam 314 falls entirely on and substantially perpendicular to second tang surface 302. By ensuring that axis 315 is substantially perpendicular to second tang surface 302 during operation, a maximum portion of each pulse will be detected by the acoustic receiver (i.e., by minimizing off-axis refraction). As discussed above, beam 314 preferably propagates through an acoustic coupling medium 325 (shown in FIG. 11). Each pulse in beam 314 preferably has a pressure distribution about axis 315 analogous to the pressure distribution of beam 14 shown at 50 in FIG. 5, so that as strong a signal as possible is generated across wire/commutator tang interface region 310. A pressure distribution such as that shown at 51 is less preferred.

Figure 10A:
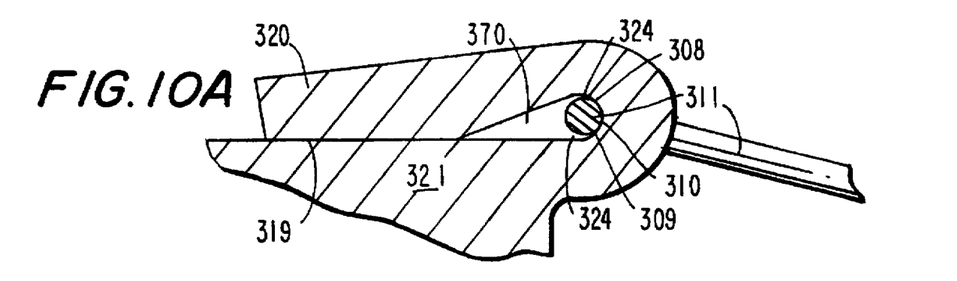
FIGS. 10A–10D are cross-sectional views of wire/commutator tang interface regions of varying quality being tested in accordance with the present invention, taken from line 10—10 of FIG. 9.
Figure 10B:
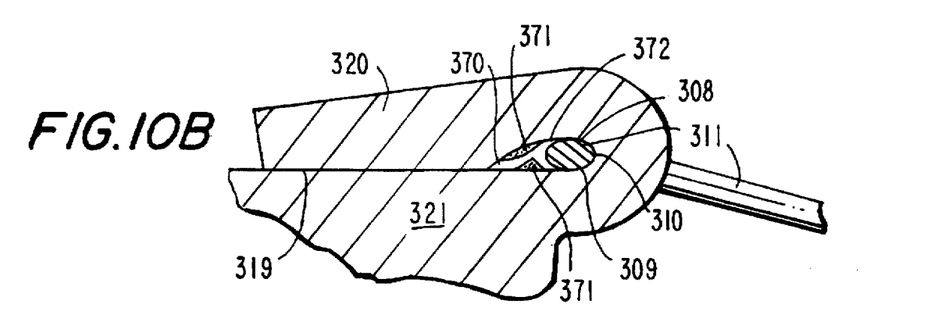
Figure 10C:
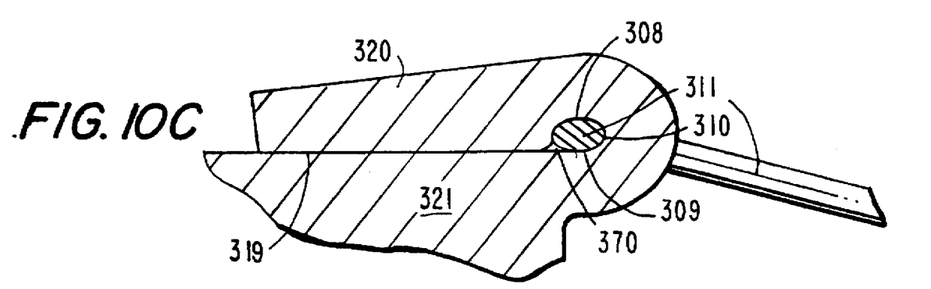
Figure 10D:
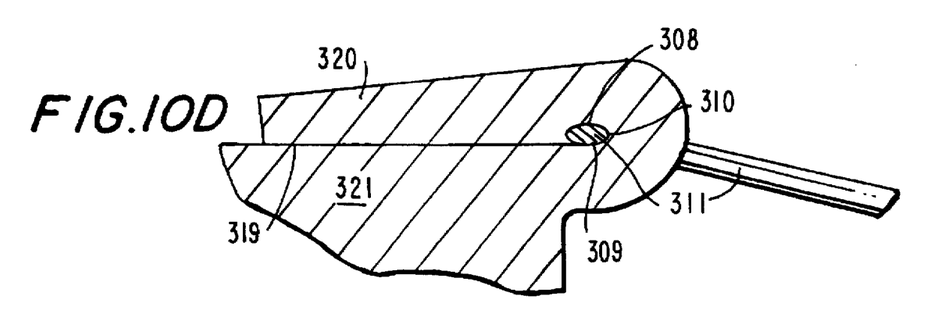

FIGS. 10A–10D illustrate several tang/commutator bar joints of varying quality. FIG. 10A, for example, shows a fused joint with an unacceptable wire/commutator tang interface region 310. Deep gaps 324 at interface regions 308 and 309 and large gap 370 indicate poor mechanical strength and poor electrical contact. FIG. 10B illustrates another fused joint with a wire/commutator tang interface region 310 in which residual unmelted insulation 372 and partially vaporized and redeposited insulation 371 remain in gaps 324 and 370. FIG. 10C illustrates a fused joint with an ideal wire/commutator tang interface region 310. In this region, there are no large gaps or residual insulation that interfere with electrical conductivity between wire 311 and commutator tang 320. The ideal interface region probably still has gap 370, but its size is small and contains only air—indicating that the heat and pressure were applied correctly during fusing. Finally, FIG. 10D depicts a fused joint in which the armature wire has been excessively deformed (i.e., flattened). As described more fully later, excessive wire deformation is indicative of excessive heat or pressure during the fusing process. An excessively deformed armature wire may be mechanically weak and, in addition, a portion of the wire not within the bent commutator tang may have an exposed conductive surface—i.e., posing a risk of short circuiting.

Figure 11:
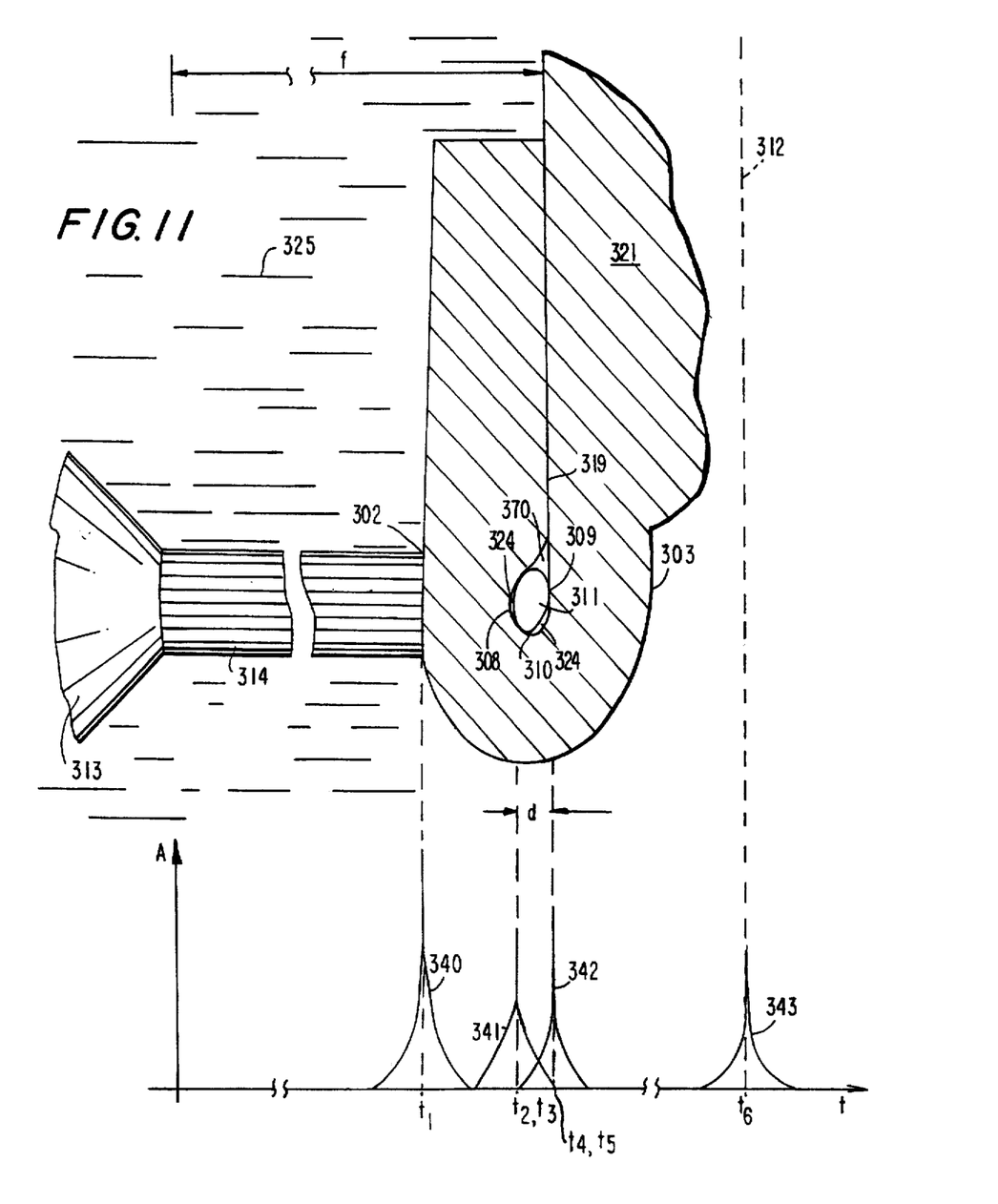
FIG. 11 is a fragmentary cross-sectional view of a wire/commutator tang interface region being tested in accordance with the present invention, taken from line 11—11 of FIG. 9, showing a graphical representation of the acoustic signature reflected by the joint.

As shown in FIG. 11, the apparatus of the invention transmits acoustic pulses at times spaced apart sufficiently for each pulse to return to probe 313 before the next pulse is sent. The spacing is based on the expected maximum round-trip time for a pulse. Each pulse in beam 314 is partially reflected by surface 302, giving rise to detected pulse 340 at a time interval $t_1$ from the time of transmission, which is correlated to the distance between probe 313 and surface 302. Some portion of each pulse passes through surface 302 and reflects off gaps 324 in interface region 308, giving rise to a detected pulse 341 at a time interval $t_2$ from the time of transmission, which is correlated to the distance between probe 313 and interface region 308. Some portion of each pulse passes through surface 302 and interface region 308 and reflects off gaps 324 in interface region 309, giving rise to a detected pulse 342 at a time interval $t_4$ from the time of transmission, which is correlated to the distance between probe 313 and interface region 309. Finally, some portion of each pulse passes through surface 302, and interface regions 308 and 309 (either because it impinges the interface region where there are no gaps 324, or because a portion of the pulse impinging on gaps 324 is able to pass through gaps 324) and reflects off second surface 312 of commutator bar 321, giving rise to a detected pulse 343 at a time interval $t_6$ from the time of transmission, which is correlated to the distance between probe 313 and second surface 312. There are also effects caused by secondary reflections at each surface, but those can be ignored. The acoustic signature shown in FIG. 11 plots received amplitude A as a function of time t from transmission, with probe 313 spaced a distance f from interface region 309, where f is the focal length of probe 313 (i.e., interface region 309 lies in the focal plane of probe 313). Either focal length f or the position of probe 313 can be varied to accommodate the measurement of different portions of an interface region.

Figure 12A:
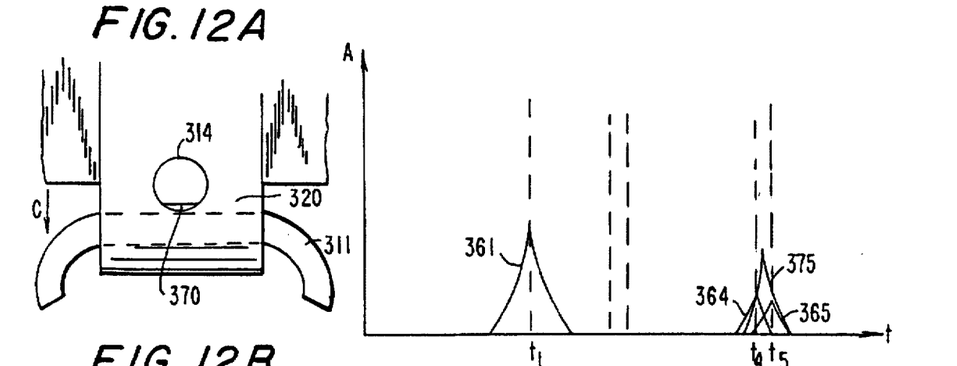
FIGS. 12A–12C are schematic representations of the acoustic beam of the present invention as it scans different locations across a wire/commutator tang interface region, showing a graphical representation of the acoustic signature reflected at each location.
Figure 12B:
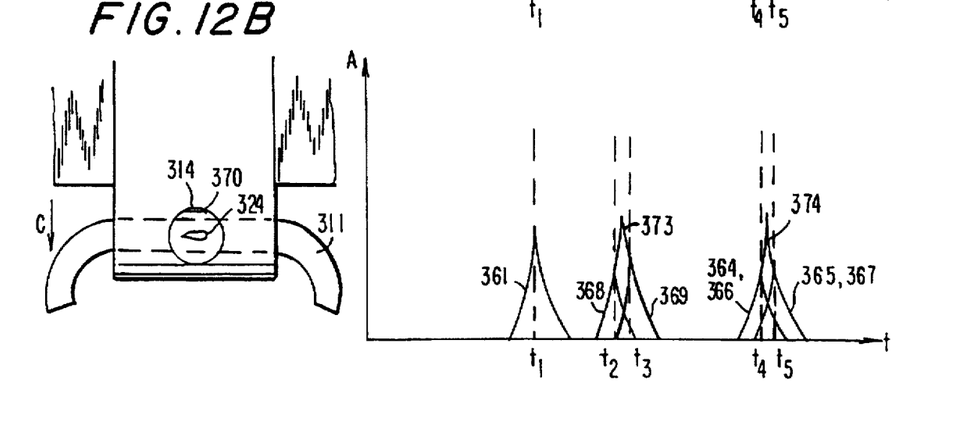
Figure 12C:
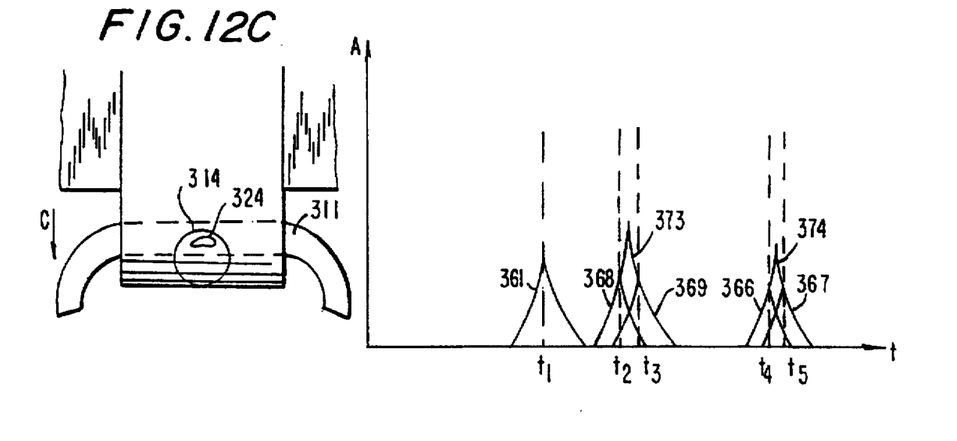

The effects of various surfaces and joints, as well as the need to have beam 314 aimed squarely at interface regions 308, 309 is illustrated in FIGS. 12A–12C. In FIG. 12A, beam 314 is directed at commutator tang 320 adjacent to wire 311, but not impinging wire 311. The corresponding acoustic signature shows the reflected amplitudes A versus time t for several reflections. At $t_1$, pulse 361 corresponds to a portion of the transmitted pulse that has reflected from second tang surface 302. At $t_4$, $t_5$ pulse 375 corresponds to a portion of the transmitted pulse that has passed through surface 302 and reflected from interface region 308 (shown in FIG. 11) between commutator tang first surface 301 and commutator bar surface 319 and from gap 370. Gap 370 is usually relatively deep (i.e., deeper than gaps 324) and located directly adjacent to wire 311. Because gap 370 is deep, two pulses 364, 365 may reflect from each side of gap 370. On the other hand, pulses 364, 365 may appear to be single pulse 375 if round-trip times $t_4$, $t_5$ are sufficiently close in magnitude.

In FIG. 12B, beam 314 is directed at commutator tang 320 directly impinging wire 311. The corresponding acoustic signature shows reflected amplitudes A versus time t for several reflections. At $t_1$, pulse 361 still corresponds to a portion of the transmitted pulse that has reflected from second tang surface 302. At $t_2$, $t_3$, pulse 373 corresponds to a portion of the transmitted pulse that has passed through surface 302 and reflected from interface region 308 between commutator tang first surface 301 and wire surface 312. If gaps 324 in interface region 308 are sufficiently deep, two distinguishable peaks 368, 369 may reflect from each of gaps 324. At $t_4$, $t_5$, pulses 366, 367 correspond to a portion of the transmitted pulse that has passed through surface 302, tang 320, and wire 311 and reflected from interface region 309 between wire surface 312 and commutator tang first surface 301. Pulses 364, 366 are reflected from different surfaces, but they both have about the same round-trip time $t_4$ because these surfaces are at the same distance f from probe 313. The same is true of pulses 365, 367. Pulses 366, 367 could appear to be single pulse 375 if round-trip times $t_4$, $t_5$ are sufficiently close. If probe 314 beam diameter is greater than wire 311 diameter, pulses 364, 365 will also appear in the plot.

FIG. 12C shows beam 314 directed to commutator tang 320, but beam 314 only impinges on commutator tang second surface 302 and interface regions 308, 309, not gap 370. Therefore, substantially the same pulses that appear at $t_1$–$t_5$ in FIG. 12B will also appear in FIG. 12C, except pulses 364, 365. In FIGS. 12A–12C, it should be clear that some portion of acoustic beam 314 may pass through tang 320, bar 321, and wire 311 and reflect off portion 303 of second tang surfaces 302 or bar surface 312. For the purpose of this invention, however, these reflections are not relevant.

If pulses 373, 374, and 375 are not distinguishable into pairs, wire thickness d is directly proportional to the time-difference between the average of round-trip times $t_2$, $t_3$, and the average of round-trip times $t_4$, $t_5$. If the pulses are distinguishable, thickness d of wire 311 is directly proportional to the time-difference between round-trip times $t_2$ and $t_4$. In either case, thickness d of wire 311 within bent tang 320 is one indicator of joint quality because d is related to the amount of heat and pressure applied to the joint during the fusing operation.

By analyzing the relative amplitudes and round-trip times of the acoustic signature, it is also possible to determine whether gaps 324 contain residual unmelted or partially vaporized and redeposited insulation. The amplitude of a portion of a pulse reflected from an interface region is, in part, directly proportional to the difference in the density of the materials at the interface. Therefore, because insulation is more dense than air, the amplitude of a pulse reflected from a metal-insulation interface is less than the amplitude of a pulse reflected from a metal-air interface. Therefore, every interface region will produce a unique acoustic signature with varying round-trip times and amplitudes. The acoustic signature may then be compared to signatures of interfaces of known quality (i.e., known gap thickness and content). A non-destructive test is therefore disclosed for testing the quality of a fused joint by determining the content and thickness of gaps 324.

FIGS. 12A–12C also show how reflected pulse amplitudes change as beam 314 is moved relative to interface region 310. By correlating the appearance and disappearance of certain reflected peaks in an acoustic signature during the relative motion between probe 313 and interface region 310, it is now possible to accurately determine the quality of every portion of interface region 310.

Apparatus 70, described above in connection with FIG. 7, can also be used to analyze the results by scanning the wire/commutator tang interface. The acoustic signature, comprising one or more reflected pulses, is received by probe 13 and fed to receiver/amplifier 72, which passes it through analog-to-digital converter 73 that creates a digitized acoustic signature for subsequent analysis. The digitized acoustic signature is passed from converter 73 to processor 77. Recognition/comparator unit 74 compares the signature to one or more predetermined acoustic signatures stored in memory 75. The result of the comparison is passed to decision unit 76 which characterizes the joint as acceptable or unacceptable. As stated above, the output of unit 76 can be used to identify a defective armature and then either discard it or require that it be re-fused. As discussed above, an acoustic signature obtained at the tang/commutator bar joint can be compared in the same way, so that the joint can be characterized as either acceptable or unacceptable.

Thus it is seen that an objective and non-destructive test of the fused joints in an armature that can be used on every armature being manufactured on an armature manufacturing line, as well as apparatus for performing that test, are provided. One skilled in the art will appreciate that the present invention can be practiced by other than the described embodiments, which are presented for purposes of illustration and not of limitation, and the present invention is limited only by the claims which follow.

What is claimed is:

1. In a manufacturing line for dynamoelectric machine armatures, an armature testing station for testing the quality of a fused joint between a commutator tang and a commutator bar in a commutator of an armature of a dynamoelectric machine, said commutator bar having first and second opposed substantially parallel commutator bar surfaces, said tang having first and second opposed substantially parallel tang surfaces and being at least partially wrapped around an armature wire having a wire surface and forming an interface region between said first tang surface and a portion of said wire surface, said joint being formed between said first commutator bar surface and said first tang surface by the application of heat and pressure to said joint in accordance with a predetermined electrical delivery function, said armature testing station comprising:

an acoustic beam emitter for directing an acoustic beam comprising at least one acoustic pulse toward said second tang surface along an axis substantially perpendicular to said second tang surface, at least a portion of each said pulse passing through said tang and reflecting off said interface region;

an acoustic receiver for measuring said reflected portion of each said at least one pulse to determine a first acoustic signature that corresponds to said interface region;

an analysis unit for comparing said first acoustic signature to a predetermined acoustic signature and for characterizing said joint as acceptable when said first acoustic signature is substantially similar to said predetermined acoustic signature; and a gripper for removing said armature from said production line, placing said armature in a location exposed to said emitter and receiver for testing, and returning said armature to said production line after testing, said gripper being rotatable to allow successive testing of each of a plurality of joints of an armature.

2. The armature testing station of claim 1 wherein said predetermined acoustic signature is determined from a second joint having a second interface region known to be of acceptable quality.

3. The armature testing station of claim 1 wherein said acoustic beam emitter is an ultrasonic beam emitter.

4. In a manufacturing line for dynamoelectric machine armatures, an armature testing station for testing the quality of a fused joint between a commutator tang and a commutator bar in a commutator of an armature of a dynamoelectric machine, said commutator bar having first and second opposed substantially parallel commutator bar surfaces, said tang having first and second opposed substantially parallel tang surfaces and being at least partially wrapped around an armature wire having a wire surface and forming an interface region between said first tang surface and a portion of said wire surface, said joint being formed between said first commutator bar surface and said first tang surface by the application of heat and pressure to said joint in accordance with a predetermined electrical delivery function, said armature testing station comprising:

an acoustic beam emitter for directing an acoustic beam comprising at least one acoustic pulse toward said second tang surface along an axis substantially perpendicular to said second tang surface, at least a portion of each said pulse passing through said tang and reflecting off said interface region;

an acoustic receiver for measuring said reflected portion of each said at least one pulse to determine a first acoustic signature that corresponds to said interface region;

an analysis unit for comparing said first acoustic signature to a predetermined acoustic signature and for characterizing said joint as acceptable when said first acoustic signature is substantially similar to said predetermined acoustic signature;

a vessel containing a medium having a greater acoustic conductivity than air; wherein:

said interface region, said emitter and said receiver are immersed in said medium; and a gripper for removing said armature from said production line, immersing said armature in said vessel for testing, and returning said armature to said production line after testing.

5. The armature testing station of claim 4 wherein said medium is a liquid.

6. The armature testing station of claim 5 wherein said liquid medium is substantially electrically nonconductive.

7. The armature testing station of claim 5 wherein said liquid medium is substantially non-oxidizing.

8. The armature testing station of claim 4 wherein said acoustic beam emitter and said acoustic receiver are combined in an acoustic probe.

9. The armature testing station of claim 4 wherein said gripper is rotatable to allow successive testing of each of a plurality of joints of an armature.

10. The armature testing station of claim 1 wherein said acoustic beam emitter and said acoustic receiver are combined in an acoustic probe.

11. A method for testing the quality of a plurality of fused joints of a commutator of an armature of a dynamoelectric machine in succession, each of said fused joints being between one of a plurality of commutator tangs and one of a plurality of commutator bars, each of said commutator bars having first and second opposed substantially parallel commutator bar surfaces, each of said tangs having first and second opposed substantially parallel tang surfaces and being at least partially wrapped around a corresponding armature wire having a wire surface and forming a plurality of interface regions between said plurality of first tang surfaces and corresponding portions of said wire surfaces, each of said fused joints being formed between a corresponding first commutator bar surface and a corresponding first tang surface by the application of heat and pressure to said joint in accordance with a predetermined electrical delivery function, said armature having a longitudinal axis and being gripped by a gripper, said plurality of joints being disposed circumferentially around said longitudinal axis of said armature, said method comprising the steps of:

directing an acoustic beam comprising at least one acoustic pulse substantially perpendicular to and substantially toward said longitudinal axis of said armature, at least a portion of each said at least one pulse passing through a first of said second tang surfaces and reflecting off a first of said interface regions;

rotating said armature around said longitudinal axis of said armature so that said acoustic beam is successively directed at each of said plurality of interface regions;

measuring said reflected portion of each said at least one pulse during said rotating to determine an acoustic signature profile, said profile consisting of a plurality of acoustic signatures, each of said plurality of acoustic signatures corresponding to an interface region of each of said plurality of fused joints;

comparing each of said plurality of acoustic signatures to a predetermined acoustic signature; and individually characterizing said plurality of fused joints as acceptable when each of said plurality of acoustic signatures is substantially similar to said predetermined acoustic signature.

12. The method of claim 11 wherein said rotating step comprises rotating said armature continuously.

13. The method of claim 11 wherein said rotating step comprises rotating said armature continuously when said acoustic beam is not reflecting off one of said plurality of interface regions and temporarily pausing said rotating when a portion of said acoustic beam is reflecting off one of said plurality of interface regions for a period of time sufficient to perform said measuring step.

14. The method of claim 11 wherein said predetermined acoustic signature is determined from a joint having an interface region known to be of acceptable quality.

15. The method of claim 11 wherein said step at directing an acoustic beam comprises directing an ultrasonic beam.

16. The method of claim 11 wherein said directing step comprises directing said beam toward said longitudinal axis of said armature through a medium having a greater acoustic conductivity than air.

17. The method of claim 16 wherein said directing step comprises directing said beam toward said longitudinal axis of said armature through a liquid medium.

18. The method of claim 17 wherein said directing step comprises directing said beam toward said longitudinal axis of said armature through a liquid medium that is substantially electrically nonconductive.

19. The method of claim 18 wherein said directing step comprises directing said beam toward said longitudinal axis of said armature through a liquid medium that is substantially non-oxidizing.

20. An apparatus for testing the quality of a plurality of fused joints of a commutator of an armature of a dynamoelectric machine in succession, each of said fused joints being between one of a plurality of commutator tangs and one of a plurality of commutator bars, each of said commutator bars having first and second opposed substantially parallel commutator bar surfaces, each of said tangs having first and second opposed substantially parallel tang surfaces and being at least partially wrapped around a corresponding armature wire having a wire surface and forming a plurality of interface regions between said plurality of first tang surfaces and corresponding portions of said wire surfaces, each of said fused joints being formed between a corresponding first commutator bar surface and a corresponding first tang surface by the application of heat and pressure to said joint in accordance with a predetermined electrical delivery function, said plurality of joints being disposed circumferentially around said longitudinal axis of said armature, said apparatus comprising:

an acoustic beam emitter for directing an acoustic beam comprising at least one acoustic pulse substantially perpendicular to and substantially toward said longitudinal axis of said armature, at least a portion of each said at least one pulse passing through a first of said second tang surfaces and reflecting off a first of said interface regions;

a gripper for gripping said armature and rotating said armature around said longitudinal axis of said armature so that said acoustic beam is successively directed at each of said plurality of interface regions;

an acoustic receiver for measuring said reflected portion of each said at least one pulse during said rotating to determine an acoustic signature profile, said profile consisting of a plurality of acoustic signatures, each of said plurality of acoustic signatures corresponding to an interface region of each of said plurality of fused joints; and an analysis unit for comparing each of said plurality of acoustic signatures to a predetermined acoustic signature and individually characterizing said plurality of fused joints as acceptable when each of said plurality of acoustic signatures is substantially similar to said predetermined acoustic signature.

21. The method of claim 20 wherein said rotating step comprises rotating said armature continuously.

22. The method of claim 20 wherein said rotating step comprises rotating said armature continuously when said acoustic beam is not reflecting off one of said plurality of interface regions and temporarily pausing said rotating when a portion of said acoustic beam is reflecting off one of said plurality of interface regions for a period of time sufficient to perform said measuring step.

23. The apparatus of claim 20 wherein said predetermined acoustic signature is determined from a joint having an interface region known to be of acceptable quality.

24. The apparatus of claim 20 wherein said acoustic beam emitter is an ultrasonic beam emitter.

25. The apparatus of claim 20 further comprising a vessel containing a medium having a greater acoustic conductivity than air; wherein:

said plurality of interface regions, said emitter and said receiver are immersed in said medium.

26. The apparatus of claim 25 wherein said medium is a liquid.

27. The apparatus of claim 26 wherein said liquid medium is substantially electrically nonconductive.

28. The apparatus of claim 26 wherein said liquid medium is substantially non-oxidizing.

29. The apparatus of claim 20 wherein said acoustic beam emitter and said acoustic receiver are combined in an acoustic probe.

30. A method for testing the quality of a fused joint between a commutator tang and a commutator bar in a commutator of an armature of a dynamoelectric machine, said commutator bar having first and second opposed substantially parallel commutator bar surfaces, said tang having first and second opposed substantially parallel tang surfaces and being at least partially wrapped around an armature wire having a wire surface and forming an interface region between said first tang surface and a portion of said wire surface, said joint being formed between said first commutator bar surface and said first tang surface by the application of heat and pressure to said joint in accordance with a predetermined electrical delivery function so that said commutator tang is softened and so that insulation on a portion of said armature wire within said softened deformed commutator tang is vaporized, said method comprising the steps of:

directing an acoustic beam comprising at least one acoustic pulse toward said second tang surface along an axis substantially perpendicular to said second tang surface, at least a portion of each said at least one pulse passing through said tang and reflecting off said interface region;

measuring said reflected portion of each said at least one pulse to determine a first acoustic signature that corresponds to said interface region;

comparing said first acoustic signature to a predetermined acoustic signature; and characterizing said joint as unacceptable when said first acoustic signature is substantially similar to said predetermined acoustic signature.

31. The method of claim 30 wherein said predetermined acoustic signature is determined from a second joint having a second interface region known to contain said insulation that has not fully vaporized.

32. The method of claim 30 wherein said predetermined acoustic signature is determined from a second joint having a second interface region known to contain said insulation that has partially vaporized and redeposited.

33. The method of claim 30 wherein said predetermined acoustic signature is determined from a second joint having a second interface region known to have at least one gap of a predetermined depth.

34. The method of claim 30 wherein said step at directing an acoustic beam along said axis comprises directing an ultrasonic beam along said axis.

35. The method of claim 30 wherein said directing step comprises directing said beam toward said second tang surface through a medium having a greater acoustic conductivity than air.

36. The method of claim 35 wherein said directing step comprises directing said beam toward said second tang surface through a liquid medium.

37. The method of claim 36 wherein said directing step comprises directing said beam toward said second tang surface through a liquid medium that is substantially electrically nonconductive.

38. The method of claim 36 wherein said directing step comprises directing said beam toward said second tang surface through a liquid medium that is substantially non-oxidizing.

39. Apparatus for testing the quality of a fused joint between a commutator tang and a commutator bar in a commutator of an armature of a dynamoelectric machine, said commutator bar having first and second opposed substantially parallel commutator bar surfaces, said tang having first and second opposed substantially parallel tang surfaces and being at least partially wrapped around an armature wire having a wire surface and forming an interface region between said first tang surface and a portion of said wire surface, said joint being formed between said first commutator bar surface and said first tang surface by the application of heat and pressure to said joint in accordance with a predetermined electrical delivery function so that said commutator tang is softened and so that insulation on a portion of said armature wire within said softened deformed commutator tang is vaporized, said apparatus comprising:

an acoustic beam emitter for directing an acoustic beam comprising at least one acoustic pulse toward said second tang surface along an axis substantially perpendicular to said second tang surface, at least a portion of each said pulse passing through said tang and reflecting off said interface region;

an acoustic receiver for measuring said reflected portion of each said at least one pulse to determine a first acoustic signature that corresponds to said interface region; and an analysis unit for comparing said first acoustic signature to a predetermined acoustic signature and for characterizing said joint as unacceptable if said first acoustic signature is substantially similar to said predetermined acoustic signature.

40. The apparatus of claim 39 wherein said predetermined acoustic signature is determined from a second joint having a second interface region known to contain said insulation that has not fully vaporized.

41. The apparatus of claim 39 wherein said predetermined acoustic signature is determined from a second joint having a second interface region known to contain said insulation that has partially vaporized and redeposited.

42. The apparatus of claim 39 wherein said predetermined acoustic signature is determined from a second joint having a second interface region known to have at least one gap of predetermined depth.

43. The apparatus of claim 39 wherein said acoustic beam emitter is an ultrasonic beam emitter.

44. The apparatus of claim 39 further comprising a vessel containing a medium having a greater acoustic conductivity than air, wherein:

said interface region, said emitter and said receiver are immersed in said medium.

45. The apparatus of claim 39 wherein said medium is a liquid.

46. The apparatus of claim 45 wherein said liquid medium is substantially electrically nonconductive.

47. The apparatus of claim 45 wherein said liquid medium is substantially non-oxidizing.

48. The apparatus of claim 39 wherein said acoustic beam emitter and said acoustic receiver are combined in an acoustic probe.

* * * * *